United States Patent [19]

Carmosin et al.

[11] Patent Number: 4,582,836
[45] Date of Patent: Apr. 15, 1986

[54] OCTAHYDROINDOLIZINE COMPOUNDS USEFUL AS ANALGESICS

[75] Inventors: Richard J. Carmosin, Red Hill; John R. Carson, Norristown, both of Pa.

[73] Assignee: McNeilab, Inc., Fort Washington, Pa.

[21] Appl. No.: 689,883

[22] Filed: Jan. 9, 1985

[51] Int. Cl.[4] .................. A61D 31/445; C07D 221/04
[52] U.S. Cl. .................................... 514/299; 514/241; 514/242; 514/254; 514/256; 544/180; 544/182; 544/238; 544/336; 546/112
[58] Field of Search ...................... 546/121, 112, 138; 514/299

[56] References Cited

PUBLICATIONS

M. E. Rogers and Joseph Sam, *Journal of Medicinal Chemistry*, 18, 1126–1130 (1975).
"A Synthesis of Octahydropyrrocolines", Francis Lions et al., *J. Pruc. Royal Soc. N.S. Wales* 73:240-252 (1940).
Reinecke et al., "The Structures and Spectral Properties . . . " Departments of Chemistry, University of California, (1966), pp. 4215-4220, vol. 31.

I. Murakoshi in *Chemical Abstracts*, vol. 52, 18409b to 18410e (1958).
Yasutaka Nagal et al., *Chem. Pharm. Bull.*, vol. 27, No. 5, pp. 1159–1168, (1979), Research Laboratory, Dainippon Phar. Co.
Stetter et al., *J. Heterocyclic Chem.*, vol., 14, pp. 573–581, (1977), "Addition von Aldehyden . . . ".

*Primary Examiner*—Henry R. Jiles
*Assistant Examiner*—Bernard I. Dentz
*Attorney, Agent, or Firm*—David J. Levy

[57] ABSTRACT

Octahydroindolizidines of the formula (I):

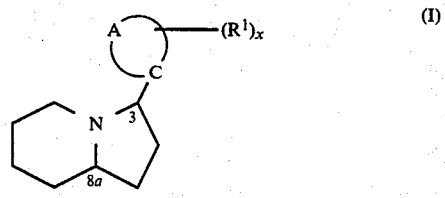

where A is a 3-7 carbon or hetero-containing ring, $R^1$ is a substituent and x is 0-3. Also, pharmaceutical composition for treating pain and methods for synthesis and use as well as novel intermediates in the synthesis.

29 Claims, No Drawings

OCTAHYDROINDOLIZINE COMPOUNDS USEFUL AS ANALGESICS

The present invention comprises certain octahydroindolizine compounds including acid addition salts thereof, methods for their preparation and use, pharmaceutical compositions and intermediates used in their synthesis. 3-Aryloctahydroindolizines are disclosed by I. Murakoshi in *Yakugaku Zasshi*, 78, pages 594–7 (1958) which appears in *Chemical Abstracts* at Volume 52, pages 18409b to 18410e (1958); by Y. Nagai et al in *Chem. Pharm. Bull.*, 27 (5), pages 1159–1168 (1979); and H. Stetter et al in the *Journal of Heterocyclic Chemistry*, 14, pages 573–581 (1977). 1-Phenylindolizine is disclosed by M. G. Reinecke et al in the *Journal of Organic Chemistry*, 31, pages 4215–4220 (1966).

SUMMARY OF THE INVENTION

Compounds of the present invention are of the following formula (I):

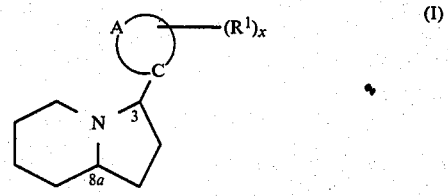

and acid addition salts wherein A represents the atoms necessary to form a 3 to 7 membered carbocyclic ring or a thienyl, furanyl, pyrrolyl, pyridinyl, pyridazinyl, pyrimidinyl, pyrazinyl or triazinyl ring, $R^1$ is a substituent and x is 0–3. Also included within the invention are pharmaceutical compositions, methods for the synthesis of formula (I) compounds and intermediates used in such syntheses.

DETAILED DESCRIPTION OF THE INVENTION

Compounds of the present invention are octahydroindolizines of the following formula (I):

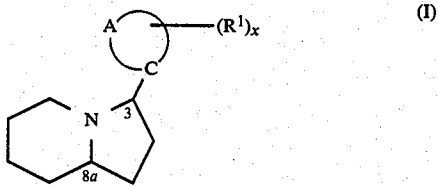

wherein

A represents the atoms necessary to form a ring system selected from the group consisting of phenyl, naphthyl, cycloalkyl, cycloalkenyl, thienyl, furanyl, pyrrolyl, pyridinyl, pyridazinyl, pyrimidinyl, pyrazinyl or triazinyl;

$R^1$ is independently cyano, halogen, alkyl, alkyloxy, alkylthio, haloalkyl, alkenyl, alkynyl or cycloalkenyl or $R^1$ is alkyl, alkenyl or alkynyl substituted by hydroxy; and x is the integer 0, 1, 2 or 3, provided that when A is phenyl, (i) x is 1, 2 or 3, and (ii) if x is 1, $R^1$ is not fluoro at the para position, and the pharmaceutically-acceptable acid-addition salts thereof.

Pharmaceutical compositions of the invention comprise the formula (I) compounds as defined above also including those wherein when A is phenyl and x is 0, and those when A is phenyl and x is 1, $R^1$ is fluro at the para position. In more detail, A is phenyl; naphthyl; cycloalkyl of about 3 to 7 carbons such as cyclopentyl and cyclohexyl; cycloalkenyl of about 3 to 7 carbons such as cyclopentenyl and cyclohexenyl, e.g. 1-cyclohexen-1-yl; thienyl such as 2- or 3-thienyl; furanyl such as 2- or 3-furanyl; pyrrolyl such as 2- or 3-pyrrolyl; pyridinyl such as 2-, 3- or 4-pyridinyl; pyridazinyl such as 3- or 4-pyridazinyl; pyrimidinyl such as 2- 4- or 5-pyrimidinyl; pyrazinyl such as 2-pyrazinyl; or triazinyl such as 1,2,3-triazinyl attached at the 4 or 5 position thereof, 1,2,4-triazinyl attached at the 3, 5 or 6 position or 1,3,5-triazinyl attached at the 2 position.

$R^1$, in more detail, is independently, e.g., two different $R^1$ moieties may be attached to the A ring when x is 2, cyano; halogen such as fluoro, chloro, bromo and iodo; alkyl of about 1 to 8 carbons such as methyl, ethyl, n-propyl and sec-butyl; alkoxy of about 1 to 8 carbons such as methoxy, ethoxy and iso-propoxy; alkylthio of about 1 to 8 carbons such as methylthio and ethylthio; haloalkyl of about 1 to 8 carbons independently substituted by one or more of fluoro, chloro, bromo or iodo such as trifluoromethyl and 2,2,2-trifluoroethyl; alkenyl of about 2 to 8 carbons such as ethenyl, 1-propenyl and 2-propenyl; alkynyl of about 2 to 8 carbons such as ethynyl, 1-propargyl and 2-propargyl; cycloalkenyl of about 3 to 7 carbons such as cyclopropenyl and 1-cyclohexenyl; or such alkyl, alkenyl or alkynyl substituted by hydroxy such as 3-hydroxy-n-butyl, 3-hydroxy-1-n-butenyl and 6-hydroxy-1-n-hexynyl.

Particular A-$R^1$ ring systems for formula (I) include phenyl rings where x is 1, 2 or 3 and $R^1$ is halogen such as ortho-halophenyl, e.g., ortho-bromophenyl, ortho, ortho-fluorochlorophenyl, and ortho,ortho-difluorophenyl, and particularly where x is 1, 2 or 3, e.g. 1, and at least one $R^1$ substituent is at the ortho position of the phenyl ring.

Particular compounds of the invention include the following:
3-(2-bromophenyl)octahydroindolizine,
3-(3-methoxyphenyl)octahydroindolizine,
3-(2-methoxyphenyl)octahydroindolizine,
3-(1-naphthyl)octahydroindolizine,
3-(4-bromophenyl)octahydroindolizine,
3-(2-chlorophenyl)octahydroindolizine,
3-(2-methylphenyl)octahydroindolizine,
3-(2-trifluoromethylphenyl)octahydroindolizine,
3-(4-n-propylphenyl)octahydroindolizine,
3-(2,4-dichlorophenyl)octahydroindolizine,
3-(3-bromophenyl)octahydroindolizine,
3-(2,6-difluorophenyl)octahydroindolizine,
3-(2,3,4-trichlorophenyl)octahydroindolizine,
3-(2,5-dichlorophenyl)octahydroindolizine,
3-(2-chloro-6-fluorophenyl)octahydroindolizine,
3-cyclohexyloctahydroindolizine,
3-(2-methylcyclohexyl)octahydroindolizine,
3-[2-(methylthio)phenyl]octahydroindolizine,
3-(2-cyanophenyl)octahydroindolizine,
3-(2,6-dichlorophenyl)octahydroindolizine,
3-(2,5-dichloro-3-thienyl)octahydroindolizine,
octahydro-3-(2-pyrazinyl)indolizine, and
3-[4-(cyclohexen-1-yl)phenyl]octahydroindolizine.

Various isomers are possible in formula (I) compounds and the present invention includes all such individual enantiomers, diasteriomers, racemates and other isomer ratios. Specifically, formula (I) compounds have 3-substitution and, may exist in the following 4 forms, the pendant 8a bond being to a hydrogen:

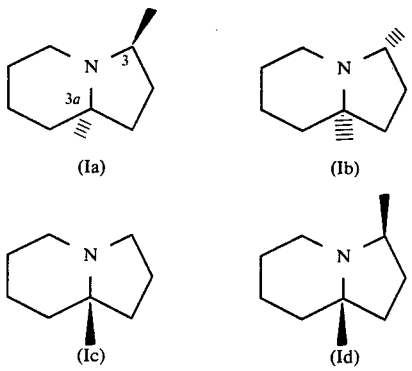

Structures (Ia) and (Ic) are enantiomers of each other as are (Ib) and (Id). In the present specification, the designation 3aα,8aβ in nomenclature of specific compounds is used for the pair (Ia) and (Ic) according to Chemical Abstracts usage, it being clear that such 3α,8aβ compound is a racemate composed of the 2 enantiomers (Ia) and (Ic). Likewise 3α,8aα is the designation of the pair of compounds having partial structures (Ib) and (Id). Resolution of enantiomers shown in the application, of course, results in a single enantiomer without its enantiomeric mirror image and these individual enantiomers are designated by (−) or (+) according to the direction in which they turn polarized light.

Compounds of this invention may be prepared via any of three Routes (A), (B) and (C).

Route (A):

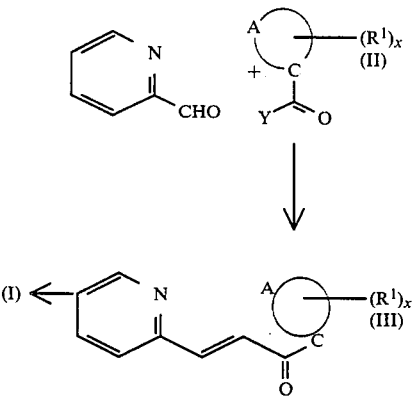

Route (B):

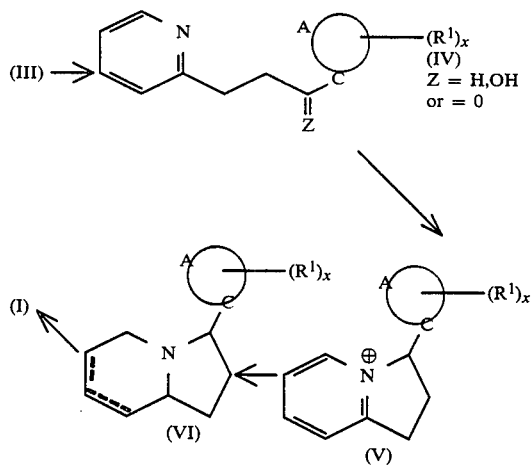

Route (C):

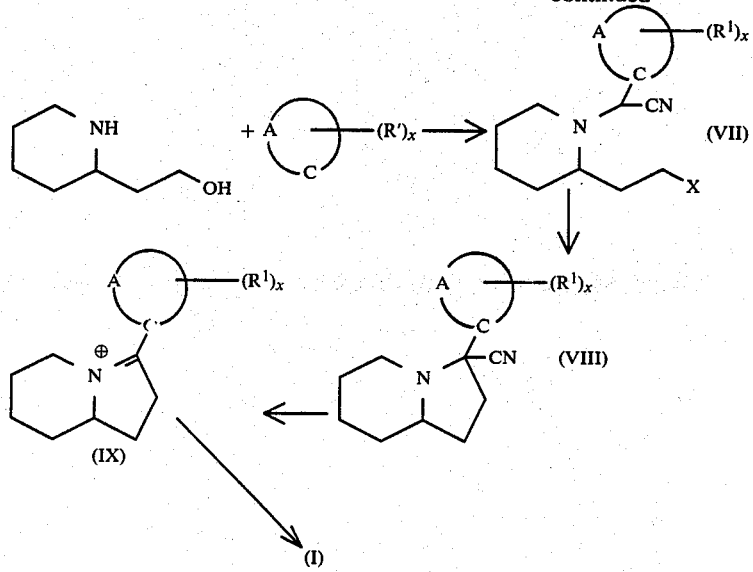

In the first Route (A), pyridine-2-carboxaldehyde is condensed with a ketone of formula (II) where Y is —CH$_3$, e.g. a substituted acetophenone or a heteroarylmethyl ketone, to afford a chalcone of structure (III). The condensation reaction may be carried out under Claisen-Schmidt conditions, for instance, in a lower alkanol solvent, at a temperature of −30° to +50° C. preferable about 10° C. in the presence of an alkali metal hydroxide. Alternatively the condensation may be brought about under Knoevenagel conditions: ammonia or a primary or secondary amine catalyst and a carboxylic acid. For instance piperidine in acetic acid at an elevated temperature of about 50° to 100° C. will effect the condensation. Catalytic hydrogenation and concurrent cyclization of the chalcone (III) under acidic conditions affords the 3-substituted octahydroindolizines (I). The hydrogenation may be carried out over noble metals e.g. platinum, palladium, rhodium or ruthenium preferably platinum or rhodium on carbon or nickel. An alkanoic acid or an lower alkanol may be used as solvent. A mineral acid such as hydrogen chloride or perchloric acid may be present to promote the reaction. The hydrogenation may be carried out at from room temperature to about 100° C. at hydrogen pressures ranging from about 30 psi to about 3000 psi. Route (A) is preferably not used if the A-ring constitutes a moiety which is sensitive to hydrogenation. Thus, Route (A) is best used when the A-ring is phenyl, naphthyl or furanyl.

Route (A) may not be employed when the group

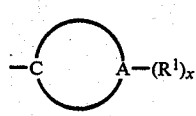

contains a group subject to catalytic hydrogenation such as a C—C double bond, a C—C triple bond, a nitrile, a pyridine ring or a thiophene ring.

When the A-C cycle is a phenyl ring, carrying out the Route (A) with exhaustive Rh catalyzed hydrogenation affords a 3-cyclohexyloctahydroindolizine.

The second Route (B) for preparation of 3-substituted octahydroindolizines (I) involves the following steps. The chalcone (III) is catalytically hydrogenated to a saturated ketone having formula (IV), where Z is =O; the ketone is then reduced to the alcohol of formula (IV) where Z is H,OH with sodium borohydride. Treatment of (IV), where Z is H,OH with hydrogen bromide, thionyl chloride, tosyl chloride or mesyl chloride gives the pyridinum salt (V). The pyridinum ring is partially reduced by the action of sodium borohydride to a mixture of olefins (VI). A mild catalytic reduction affords the 3-substituted octahydroindolizine (I).

In the third Route (C) piperidine-2-ethanol is caused to react with an aldehyde of formula (II) where Y is —H, e.g. a substituted benzaldehyde, and an alkali metal cyanide to give a hydroxynitrile (VII), X=OH. The hydroxynitrile (VII), X=OH is converted by the action of thionyl chloride, methane sulfonyl chloride or toluenesulfonyl chloride to a cyclic derivative of formula (VII) where the group X is a leaving group such as chloro, methanesulfonyl, or p-toluenesulfonyl respectively. Treatment of the cyclic derivative with a strong base, for instance, sodium hydride in DMF, gives a 3-cyano-3-substituted octahydroindolizine of formula (VIII). The conversion of a compound of formula (VIII) to the target compound of formula (I) may be carried out directly by treatment with sodium cyanoborohydride under acidic conditions or with lithium aluminum hydride. The conversion may also be carried out by treatment of the compound of formula (VIII) with perchloric acid to give an iminium salt (IX) which is transformed to the desired product (I) by catalytic hydrogenation over a noble metal catalyst, for instance platinum or by reduction with a hydride reducing agent, e.g., NaBH$_4$, NaBH$_3$CN or LiAlH$_4$.

Route (C) is preferred for compounds wherein the A-ring group is subject to catalytic reduction. For instance heteroaryl groups such as pyridine, thiophene, pyrrole and furan or for aryl groups bearing 2,6-disubstitutions.

In each of the Routes (A), (B) and (C), a mixture of diastereoisomers is produced in which the biologically more active 3α, 8αβ diastereomers, the diastereomeric pair of enantiomers bearing the hydrogens at 3 and 8a are on the same face, is predominant. The diastereomers may be separated by chromatography on silica or by fractional crystallization. If desired, the compounds of formula (I) may be resolved into optical isomers, i.e. enantiomers, by fractional crystallization of a salt with an optically active acid such as, for instance, di-p-toluoyl tartaric acid.

The groups $R^1$ may be attached directly to the —C—A function during the synthesis of the octahydroindolizine ring. Alternatively they may be attached following the synthesis of the 3-substituted octahydroindolizine. For instance a 3-(halophenyl) octahydroindolizine may be converted to the corresponding lithium derivative by reaction with an alkyllithium. 3-(2-Lithiophenyl)octahydroindolizine on reaction with dimethyldisulfide affords 3-(2-methylthiophenyl)octahydroindolizine. Reaction of the lithio derivative with cyclohexanone affords the derivative with a 1-cyclohexanol attached. A 3-(2-halophenyl)octahydroindolizine, when subjected to palladium catalyzed coupling with cuprous cyanide or a 1-alkyne gives the corresponding cyano or alkynyl derivative.

Compounds of formula (I) wherein the A-ring is cyclohexyl or substituted cyclohexyl may be prepared by catalytic hydrogenation of the appropriate phenyl compound over a noble metal catalyst, for example rhodium, ruthenium or platinum.

The activity of compounds of the invention as analgesics may be demonstrated by an abdominal constriction assay, a tail flick assay or a hot plate assay as described below:

Mouse Acetylcholine-Bromide-Induced Abdominal Constriction Assay: The mouse acetylcholine-induced abdominal constriction assay, as described by Collier et al. in *Brit. J. Pharmacol.* Chemother, 32:295–310, 1968, with minor modifications was one test used to assess analgesic potency. The test drugs or appropriate vehicle were administered orally (p.o.) and 30 minutes later the animals received an intraperitoneal (i.p.) injection of 5.5 mg/kg acetylcholine bromide (Matheson, Coleman and Bell, East Rutherford, NJ). The mice were then placed in groups of four into glass bell jars and observed for a ten minute observation period for the occurrence of a writhe (defined as a wave of contriction and elongation passing caudally along the abdominal wall, accompanied by a twisting of the trunk and followed by extension of the hind limbs). The percent inhibition of writhing (equated to % analgesia) was calculated as follows: The % Inhibition of writhing, i.e., % analgesia is equal to the difference between the No. of control animals writhing and the No. of drug-treated animals writhing times 100 divided by the No. of control animals writhing.

At least 20 animals were used for control and in each of the drug treated groups. Four doses were used to determine each dose response curve and $ED_{50}$ (that dose which inhibits writhing by 50%). The $ED_{50}$ values and their 95% fiducial limits were determined by a computer assisted probit analysis.

Rat Air-Induced Abdominal Contriction Assay: The rat air-induced abdominal contriction assay described by Von Voightlander and Lewis in Drug Development Research 2:577–581, 1982 was used to assess analgesic potency. The test drugs or appropriate vehicle were administered orally (p.o.) and 30 minutes later the animals received an i.p. injection of air (10 ml equivalent). The rats are then placed into individual perflex observation chambers and observed for 30 minutes for the occurrence of a writhe (defined as for the mouse). The percent inhibition of writhing (equated to % analgesia) was calculated as described above. At least 10 animals were used for control and in each of the drug-treated groups. Three to five doses were used to determine each dose response curve and $ED_{50}$ (as defined above). $ED_{50}$ values and 95% fiducial limits were determined as described above.

Mouse/Rat Tail Flick Assay: The tail flick assay, originally described by D'Amour and Smith in *J. Pharmacol. Exp. Ther.* 72:74–79, 1941 with modifications, see Vaught and Takemori, *J. Pharmacol. Exp. Ther.* 208:86–90, 1979 was used to assess analgesic potency. An animals' (mouse or rat) tail is place in the path of a focused beam of light produced by an ITTC, Inc. Mod-33 Analgesia Meter. The animal responds to this noxious stimulus produced by the beam of light by "flicking" or removing its tail from the path of the stimulus. The timer and light is manually shut off when the animal responds in such a manner. The reaction time is recorded. At appropriate times following drug administration (by the desired route) the above procedure is repeated and these reaction times compared to pre-drug reaction times. A reaction time for drug-treated animals greater than three standard deviations from the mean of the control reaction times for all the animals in the group was the criterion for an analgesic response. At least three doses with 10 animals per dose were used to construct dose response curves. A SAS Probit Analysis was used to generate $ED_{50}$ (that dose which produces analgesia in 50% of the animals) values and 95% fiducial limits (as described previously).

Mouse/Rat Hot Plate Assay: The hot plate assay was one test used to assess analgesic potency, see Vaught and Chipkin, *Eur. J. Pharmacol.* 79, 167–173, 1982 and references therein. In these experiments the hot plate apparatus (Technilab Instruments, Inc.) was maintained at $48 \pm 0.05°$ C. The response measure was the time interval between the animal being placed on the heated surface and licking or shaking its hindpaw. Test drug was administered by the desired route, and at appropriate times following drug administration, reaction times redetermined. The criterion for an analgesic response and the method for calculation of $ED_{50}$ and 95% fiducial limits is as that described for the tail flick assay. Animals: In all experiments male, virus-free, Swiss CD-1 mice (18:24 g) or male, virus-free, Wistar Rats (90–210 g) purchased from Charles River Breeders were used. They were allowed food and water ad libitum and were used only one.

In the Mouse Acetylchloine Assay described above, the compound produced in Example 20e had an $ED_{50}$ of about 3.5 mg/kg of body weight, p.o.; the compound produced in Example 10 of about 22.4 mg/kg, p.o.; and the compound produced in Example 1b of about 20 mg/kg, p.o.

In the Mouse Air-Induced Writhing Assay, the compound of Example 26 had an $ED_{50}$ of about 19.1 mg/kg of body weight, p.o. and the compound of Example 1b. about 48.6 mg/kg, p.o.

In the Mouse Tail Flick Assay, the compound produced in Example 1b had $ED_{50}$ values in different studies of about 27 to 44 mg/kg of body weight, i.p.

In the Mouse Hot Plate Assay, the compound produced in Example 1b had $ED_{50}$ values in different studies of about 27 to 35 mg/kg of body weight, i.p. while the compound of Example 26 had an $ED_{50}$ of about 16.5 mg/kg, i.p. In the Rat Hot Plate Assay, the compound of Example 10 had an $ED_{50}$ of about 22.0 mg/kg, i.p.

Based on the above results, compounds of the invention may be used to treat mild to moderately severe pain in warm-blooded animals such as humans in a manner similar to the use of meperidine hydrochloride by administration of an analgesically effective dose. The dosage range would be from about 10 to 3000 mg, in particular about 25 to 1000 mg or about 100 to 500 mg, of active ingredient 1 to 4 times per day for an average (70 kg) human although it is apparent that activity of individual compounds of the invention will vary as will the pain being treated.

To prepare the pharmaceutical compositions of this invention, one or more compounds or salt thereof of the invention as the active ingredient, is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., table, capsule, powder, injection, teaspoonful and the like, from about 10 to about 500 mg of the active ingredient.

In the following Examples and throughout the specification, the following abbreviations may be used: mg (milligrams); g (grams); kg (kilograms); ml (milliliters); mmole (milli moles); M (molar); N (normal); psi (pounds per square inch); mp (melting point); bp (boiling point); meg (milliequivalents); E (trans); Z (cis); Et$_2$O (diethyl ether); EtOAc (ethyl acetate); MeOH (methanol); EtOH (ethanol); LAH (lithium aluminum hydride); THF (tetrahydrofuran); DMF (dimethylformamide); p.o. (per os, orally); i.p. (intraperitioneal); hplc (high pressure liquid chromatography; hr (hours); min (minutes); and C,H,N,O, etc. (the chemical symbols for the elements). Unless otherwise indicated, all temperatures are reported in C (degrees centigrade) and all references to ether are to Et$_2$O.

EXAMPLE 1 a. 1-(2-Bromophenyl)-3-(2-pyridinyl)-2-propen-1-one. A 75 g (0.7 mole) sample of pyridine-2-carboxaldehyde was added in portions to a solution of 150 ml of 10% NaOH and 75 ml MeOH at 10° C. A 75 g (0.377 mole) sample of o-bromoacetophenone was added dropwise over 90 min. with stirring. The mixture was stirred for another 90 min at 11°. The mixture was partitioned between water and ether. The ether layer was washed with brine, dried (MgSO$_4$) and the solvent evaporated in vacuo. The residual oil crystallized and was recrystallized from 2-propanol to give 53 g (50% yield) of 1-(2-bromophenyl)-3-(2-pyridinyl)-2-propen-1-one, mp 67–69 C.

b. 3α-(2-Bromophenyl)-8aβ-octahydroindolizine hydrochloride (Formula (I): A=phenyl; R$^1$=2-Br; x=1). A solution of 188 g (0.65 mole) of 1-(2-bromophenyl)-3-(2-pyridinyl)-2-propen-1-one in 600 ml of glacial acetic acid was hydrogenated over 20 g of 5% rhodium on carbon at 60 psi for 3 days. The reduction was recharged with 10 g of 5% rhodium on carbon. The hydrogenation was continued for 6 hours. The catalyst was filtered and the solvent evaporated in vacuo. The residue was partitioned between Et$_2$O and 3N sodium hydroxide. The ether layer was washed with brine, dried (K$_2$CO$_3$) and the solvent evaporated in vacuo to give 157 g of a brown oil. The oil was distilled in a kugelrohr over a 115°–160° C. range at 0.5 mm/Hg to give 143 g of an oil. The oil was chromatographed in two batches on a Waters Prep 500 preparative hplc unit using 95% hexane, 5% Et$_2$O as eluant. The first major compound bearing fractions were pooled and the solvent evaporated in vacuo to give 125 g of an oil. The hydrochloride salt was prepared from MeOH-acetonitrile-hydrogen chloride and crystallized after evaporation of the MeOH. There was obtained 102 g of the title compound as a white solid in two crops, mp 210°–217° C. (72% yield). Further recrystallization from acetonitrile afforded material mp 211°–215° C.

c. 3α-(2-Bromophenyl)-8aα-octahydroindolizine Hydrochloride (Formula (I): A=phenyl; R$^1$=o-Br; x=1). The preparative hplc columns from the foregoing Example 1b, following the elution of the first component, were eluted with Et$_2$O. There was obtained after evaporation of solvent 1.64 g of oil. The hydrochloride salt was prepared from MeOH, ether, hydrogen chloride and the solvent evaporated. The residue was crystallized from acetonitrile to give the title compound as a white solid 1.22 g, mp 188°–190° C.

EXAMPLES 2–10

Following the procedure of Example 1a and employing an equivalent quantity of the appropriate methylketone of formula (II) where Y is —CH$_3$ in place of o-bromoacetophenone, the following 1-(aryl)-3-(2-pyridyl)-2-propen-1-one compounds of formula (III), analogous to the product of Example 1a were obtained represented below as Examples 2a–10a. Subsequent hydrogenation of these products from Examples 2a–10a over the indicated catalyst using the procedure of Example 1b, afforded 3-aryloctahydroindolizines of the 3α,8aβ stereochemical family of the formula (I), designated below as the products of Examples 2b–10b:

| Example | —A—(R$^1$)x | mp °C. (Form) | Catalyst |
|---|---|---|---|
| 2a | 3-CH$_3$O—phenyl | 71–73 (base) | — |
| 2b | 3-CH$_3$O—phenyl | 133–134 (HCl) | Pt |
| 3a | 2-CH$_3$O—phenyl | 76–78 (base) | — |
| 3b | 2-CH$_3$O—phenyl | 202–204 (HCl) | Pt |
| 4a | 1-naphthyl | | — |
| 4b | 1-naphthyl | 262–264 (HCl) | Pt |
| 5a | 4-Br—phenyl | 208–210 (HCl) | — |
| 5b | 4-Br—phenyl | 234–6 (HCl) | Pt |
| 6a | 2-Cl—phenyl | 147–152 (HCl) | — |
| 6b | 2-Cl—phenyl | 221–3 (HCl) | Rh |
| 7a | 2-CH$_3$—phenyl 145–9 (HCl) | | |
| 7b | 2-CH$_3$—phenyl | 205–8 (HCl) | Pt |

-continued

| Example | —A—(R¹)x | mp °C. (Form) | Catalyst |
|---|---|---|---|
| 8a | 2-CF₃—phenyl | yellow solid (HCl) | — |
| 8b | 2-Cf₃—phenyl | 183-5 (HCl) | Pt |
| 9a | 4-n-C₃H₇—phenyl | 56-60 (base) | — |
| 9b | 4-n-C₃H₇—phenyl | 158-61 (HCl) | Pt |
| 10a | 2,4-diCl—phenyl | 63-65 (base) | — |
| 10b | 2,4-diCl—phenyl | 238-40 (HCl) | Rh |

EXAMPLE 11 a. b 1-(3-Bromophenyl)-3-(2-pyridinyl)-2-propen-1-one (Formula (III): A=phenyl, $R^1$=3-Br, x=1). A solution of 17.7 g (0.208 mole) of piperidine in 16.8 ml (0.294 mole) of glacial acetic acid was cooled to 5° C. and 51.2 g (0.47 mole) of pyridine-2-carboxaldehyde was added followed by 49 g (0.239 mole) of m-bromoacetophenone. The mixture was heated on a steam bath under $N_2$ for 25 min. The reaction was cooled and dissolved in EtOAc. The solution was washed with NaHCO₃ solution and brine and dried (MgSO₄). The solution was filtered through 450 g of SiO₂ and the SiO₂ washed with EtOAc. The solvent was evaporated in vacuo and the residue recrystallized from 2-propanol twice to give 44.6 g (63% yield) of the title compound as a yellow solid, mp 98°-110° C.

b. 3α-(3-Bromophenyl)-8aβ-octahydroindolizine Perchlorate (Formula (I): A=phenyl; $R^1$=3-Br; x=1). A solution of 43.6 g (0.151 mole) of 1-(3-bromophenyl)-3-(2-pyridinyl)-2-propen-1-one in 200 ml of glacial acetic acid was hydrogenated at 60 psi over 4.67 g of 5% rhodium on carbon for 2 days. The catalyst was filtered and the solvent evaporated in vacuo. The residue was dissolved in $CH_2Cl_2$ and washed with sodium hydroxide solution and brine. It was dried ($K_2CO_3$) and the solvent evaporated in vacuo to give 34.6 g of a brown oil. A perchlorate salt was prepared from 70% perchloric acid, acetonitrile and Et₂O. There was obtained 15.05 g of solid in two crops. The solid was recrystallized twice from 2-propanol to give 9.75 g (21% yield) of the title compound as a white crystalline solid, mp 195°-198° C.

EXAMPLES 12-15

Following the procedure of Example 11a and employing an equivalent quantity of the methyl ketone of formula (II) where Y is —CH₃ in place of 3-bromoacetophenone, the following 1-aryl-3-(2-pyridinyl)-2-propen-1-ones of formula (III) analogous to the product of Example 11a were obtained represented below as Examples 12a-15a. Subsequent hydrogenation of these products from Examples 12a-15a over 5% Rh on C using the procedure of Example 11b, afforded 3-aryl-octahydroindolizines of Examples 12b-15b.

| Example | -A-(R¹)x | mp °C. (Form) |
|---|---|---|
| 12a | 2,6-difluorophenyl | 149-53 (HCl) |
| 12b | 2,6-difluorophenyl | 228-31 (HCl) |
| 13a | 2,3,4-trichlorophenyl | 98-100 (base) |
| 13b | 2,3,4-trichlorophenyl | 219-236 (decomp) (HCl) |
| 14a | 2,5-dichlorophenyl | 180-190 (HCl) |
| 14b | 2,5-dichlorophenyl | 230-242 (decomp) (HCl) |
| 15a | 2-chloro-6-fluorophenyl | 70-72 (base) |
| 15b | 2-chloro-6-fluorophenyl | 205-210 (HCl) |

EXAMPLE 16

3α-Cyclohexyl-8aβ-octahydroindolizine Hydrochloride (Formula (I): A=cyclohexyl; x=0). A solution of 20 g of 1-phenyl-3-(2-pyridinyl)-2-propen-1-one of formula (III) in 96 ml of glacial acetic acid was hydrogenated in a Parr Shaker at 60 psi over 2.95 g 5% Rh on carbon. The hydrogenation was continued for 13 days. Additions of 2.95 g of 5% Rh on carbon were made on days 2, 3, and 4. On day 5 5.9 g of 5% Rh on carbon was added. The catalyst was filtered and the solvent evaporated in vacuo. The residue was partitioned between Et₂O and NaOH solution. The ether was washed with brine, dried ($K_2CO_3$) and evaporated. The residue was distilled in a kugelrohr from 110° to 160° C., 1.2 mm Hg, to give 9.89 g of an oil. The oil was chromtographed on a Waters Prep 500 preparative hplc using 5% EtOAc, 95% hexane an eluant. The first major compound bearing fractions were pooled and the solvent evaporated to give 3.45 g of an orange oil. A hydrochloride salt was prepared from MeOH-EtOAc-hydrogen chloride. The solid was recrystallized twice from $CH_2Cl_2$—THF to give 2.74 g (14% yield) of the title compound as a white solid. mp 199°-202° C. (decomposition).

EXAMPLE 17

3-(2-Methylcyclohexyl)octahydroindolizine Hydrochloride (Formula (I): A=cyclohexyl; R=2—CH₃; x=1). A solution of 11.0 g (0.043 mole) of 1-(2-methylphenyl)-3-(2 pyridinyl)-2-propen-1-one in 100 ml of glacial acetic acid was hydrogenated at 50 psi in a Parr shaker over 2.6 g 5% Rh on carbon. Hydrogenation was continued for 5 days. Additional 2.6 g samples of 5% Rh on carbon were added on days 2, 3 and 4. The mixture was made basic with NaOH and extracted with Et₂O. The ether was dried (MgSO₄) and evaporated in vacuo. The residue was flash chromatographed on SiO₂ using EtOAc:hexane 5:95 as eluant. Fractions corresponding to the third component to emerge were pooled and the solvent evaporated in vacuo. A hydrochloride salt was prepared from ether-hydrogen chloride and was recrystallized from 2-propanol-ether to give 360 mg (3.2% yield) of the title compound, mp 197°-198.5°.

EXAMPLE 18

3α-[2-(Methylthio)phenyl]-8aβ-octahydroindolizine Hydrobromide (Formula (I): A=phenyl; $R^1$=CH₃S—; x=1. A solution of 29.8 ml (0.048 mole) of 1.6M n-butyllithium in hexane was added over 5 min to a solution of 8.9 g (0.0317 mole) of the free base of 3α-(2-bromophenyl)-8aβ-octahydroindolizine, the product of Example 1b, in 300 ml anhydrous Et₂O under $N_2$. The mixture was stirred for 2 hours. An additional 20 ml (0.031 mole) of 1.6M butyl lithium was added. The mixture was stirred for 50 min. A 10 ml (0.11 mole) sample of dimethyldisulfide was added after cooling the reaction to 5° C. The reaction was stirred at room temperature for 16 hours. The mixture was partitioned between ether and water. The ether layer was washed with brine, dried ($K_2CO_3$) and the solvent evaporated in vacuo. The oily residue was further concentrated under reduced pressure (0.5 mm Hg) for 4 hours. A hydrobromide salt was prepared from t-butanol and recrystallized twice from MeOH-t-butanol to give 7.4 g (71% yield) of the title compound as a white solid, mp 197.5°-200° C.

EXAMPLE 19

3α-(2-Cyanophenyl)-8aβ-octahydroindolizine Hydrochloride (Formula (I): A=phenyl; R$^1$=cyano; x=1). To a solution of 8.0 g (0.0286 moles) of 3α-(2-bromophenyl) 8aβ-octahydroindolizine, the product of Example 16, in 29 ml of dry pyridine under Ar was added 3.84 (0.042 mole) of cuprous cyanide and 0.15 g (0.129 mmole) of tetrakis(triphenylphosphine)palladium (0). The mixture was heated under reflux for 65 hrs. The reaction mixture was partitioned between Et$_2$O and concentrated ammonia. The ether layer was washed with ammonia and brine and dried (K$_2$CO$_3$). The solution was filtered through celite and the solvent evaporated in vacuo to give 5.6 g of a brown oil. A hydrochloride salt was prepared from ethereal HCl—CH$_3$CN and recrystallized twice from MeOH—CH$_3$CN to give 4.36(58% yield) of the title compound as a white crystalline solid mp 236°–239° C.

EXAMPLE 20 a. 2,6-Dichloro-α-[2-(2-hydroxyethyl)-1-piperidinyl]-benzeneacetonitrile. A 71.5 g (0.31 mole) sample of 2,6-dichlorobenzaldehyde was added over 45 min to a solution of 40 g of 2-piperidineethanol (0.31 mole) and 20.2 g of KCN(0.31 mole) in 100 ml of 3N HCl. The mixture was stirred for 16 hours at room temperature. The mixture was extracted with ether. The ether extract was washed with brine, dried (K$_2$CO$_3$) and the solvent evaporated in vacuo. The oily residue was triturated twice with hexane and the hexane decanted. There was obtained 80.6 g (83% yield) of the crude title compound as an oil.

b. 2-[1-[(Cyano)(2,6-dichlorophenyl)methyl]2-piperidinyl]ethyl 4-Methylbenzenesulfonate (Formula (VII)). A 49.0 (0.257 mole) sample of p-toluenesulfonyl chloride was added in portions to a cooled solution of 80.6 g (0.257 mole) of the crude product of Example 20a in 83 ml of pyridine so that the temperature was maintained between 5° and 10° C. The mixture was stirred with cooling for 2.5 hours and allowed to warm to room temperature of 16 hours. The mixture was partitioned between ether and NaHCO$_3$ solution. The ether solution was washed with brine, 4 portions of 1N HCl and 3 portions of 3N HCl. The ether was charcoaled, dried (MgSO$_4$) and the solvent was evaporated in vacuo. There was obtained 66.3 g (55% yield) of the crude title compound as an orange oil.

c. 3-Cyano-3-(2,6-dichlorophenyl)octahydroindolizine (Formula (VIII)). A solution of 64.2 g (0.137 mole) of the product of Example 20b in 342 ml of dry DMF was added dropwise over 15 min to a suspension of 0.137 mole of sodium hydride (from 6.60 g of 50% sodium hydride from which the oil had been washed with ether) under Ar. The temperature was maintained between 20° and 30° C. by cooling with an ice bath. The reaction was stirred for one hour at room temperature. The mixture was cautiously added to brine and extracted with ether. The ether solution was washed with brine and dried (MgSO$_4$). The solution was filtered through Celite and the solvent evaporated to give 42.1 g of the crude title compound as a red brown oil.

d. 3-(2,6-Dichlorophenyl)-1, 5, 6, 7, 8, 8a-hexahydro-2H-indolizinium Perchlorate (Formula (IX)). A 13.0 ml (0.151 mole) sample of 70% aqueous perchloric acid was added to a solution of 42.1 g (0.142 mole) of the product of Example 20c in 400 ml of 2-propanol. The atmosphere over the reaction was flushed with N$_2$ into a sodium hypochlorite trap. After 16 hours the solid was collected and recrystallized from MeOH-2-propanol. There was obtained 27.2 g (52% yield) of the title compound as a solid mp 133°–141° C.

e. 3α-(2,6-Dichlorophenyl)-8aβ-octahydroindolizine Hydrochloride (Formula (I): A=phenyl; R$^1$=2,6-diCl; x=2). A 6.9 g (0.11 mole) sample of sodium cyanoborohydride was added to a suspension of 27.0 g (0.073 mole) of the product of Example 20d in 73 ml of MeOH. Methanolic hydrogen chloride was added over 20 min until the pH stayed between 3 and 4. After one hour an additional 4.6 g (0.07 mole) of sodium cyanoborohydride was added and the pH again adjusted to 3 to 4. The reaction was stirred for 16 hrs. The mixture was acidified by addition of 3N HCl and stirred until bubbling ceased. The mixture was made basic by addition of NaOH solution and extracted with ether. The ether solution was extracted 3 times with 1N HCl. The HCl extract was washed with ether and made basic by addition of 50% NaOH/ice. The mixture was extracted with ether. The ether extract was washed with brine, dried (K$_2$CO$_3$) and concentrated to dryness in vacuo to give 1. g of an oily residue. The residue was chromatographed on a Waters Prep 500 hplc, eluting with 5% ether in hexane. The first fraction was concentrated to dryness in vacuo. A hydrochloride salt was prepared from the resulting oil from CH$_3$CN-hydrogen chloride. The solid was filtered and a second crop taken from ether-2-propanol. The combined crops were recrystallized from ether-CH$_3$CN to give 14.0 g (63% yield) of the title compound as a white solid, m.p. 206°–208° C.

EXAMPLE 21

3α-(2,6-Dichlorophenyl)-8aα-octahydroindolizine Hydrochloride (Formula (I): A=phenyl, R$^1$=2,6-diCl, x=2). The second compound bearing fraction from the chromatography of the foregoing Example 20e, was concentrated to dryness in vacuo. A hydrochloride salt was prepared from CH$_3$CN—hydrogen chloride. It was recrystallized from CH$_3$CN to give 0.47 g of the title compound as a crystalline solid mp 203°–206° C.

EXAMPLE 22 a. 1-(2,5-Dichloro-3-thienyl)-3-(2-pyridinyl)-2-propen-1-one (Formula (III)). To 7.9 ml (0.08 mole) of piperidine under nitrogen with cooling in an ice bath was added glacial acetic acid (6.48 ml; 0.108 mole) portionwise. Then pyridine-2-carboxaldehyde (19.7 g; 0.184 mole) and 18 g (0.09 mole) of 2,5-dichloro-3-acetylthiophene was added. The mixture was heated for 1.5 hours with mechanical stirring under nitrogen at 60°–70° C. The reaction was cooled to room temperature and then ice water added. The yellow solid product was filtered and recrystallized from isopropanol. After air drying, 17.8 grams (68% yield) of the title compound was obtained. mp 88°–90° C.

b. 1-(2,5-Dichloro-3-thienyl)-3-(2-pyridinyl)-1-propanone (Formula (IV)). The product of Example 22a (7.8 g; 0.027 mole) was dissolved in 80 ml of glacial acetic acid and 15 mg of platinum oxide added. The mixture was shaken on a Paar apparatus under 50 psi of hydrogen for 3 hours. An additional 325 mg of platinum oxide was added and shaken on the Paar apparatus at 50 psi of hydrogen overnight. The acetic acid was stripped off under reduced pressure and the oily residue treated with 10% aqueous sodium hydroxide and extracted with ether. The ether extracts were combined, dried over anhydrous magnesium sulfate and the ether stripped off to give 6 g (78% yield) of a light green oil.

c. 1-(2,5-Dichloro-3-thienyl)-3-2-pyridinyl)-1-propanol (Formula (IV)). The product of Example 22b (6 g; 0.021 mole) was dissolved in 60 ml of absolute methanol and sodium borohydride (2.4 g; 0.062 mole) added in portions with stirring under nitrogen. It was allowed to stir overnight at ambient temperature. Hydrochloric acid (3N) was added to destroy any unreacted sodium borohydride. After all bubbling had ceased, the solution was concentrated in vacuo. Then 3N aqueous sodium hydroxide was added until the solution was basic, then extracted with ether. The ether extracts were combined, dried over magnesium sulfate, and evaporated to an oily residue (5.3 g; 80% yield).

d. 3-(2,5-Dichloro-3-thienyl)-1,2,3,5,8,8a (and 1,2,3,5,6,8a)hexahydroindolizine (Formula (VI)). The product of Example 22c (5.3 g, 0.018 mole) was dissolved in 50 ml of dry chloroform and 4.5 ml of ethyl diisopropylamine (0.026 mole) added. The solution was cooled to 50° C. in an ice bath under nitrogen, and a solution of thionyl chloride (1.9 ml, 0.026 mole) in 10 ml of chloroform was added dropwise with stirring. After the addition was completed (keeping the reaction mixture at 5°–10° C.), the mixture was stirred for 2 hours at room temperature. The chloroform was evaporated in vacuo at room temperature and then 100 ml of water was added to the oil residue. The mixture was triturated with water, and the aqueous solution (yellow) carefully decanted away from insoluble material. To this aqueous solution under nitrogen was added 6.1 g of sodium borohydride in portions then allowed to stir overnight at room temperature. Hydrochloric acid (3N) was added to destroy unreacted sodium borohydride, then made basic with 12% sodium hydroxide, and extracted with ether. The ether extracts were dried over MgSO$_4$, and the ether evaporated in vacuo to give 3.8 g of an oily residue (78% crude yield).

e. 3-(2,5-Dichloro-3-thienyl)octahydroindolizine Hydrochloride (Formula (I): A=3-thienyl; R$^1$=2,5-diCl; x=2). The product of Example 22d (3.8 g, 0.0139 mole) was dissolved in 50 ml of glacial acetic acid and 235 mg of platinum oxide added. The mixture was shaken on a Paar apparatus under 50 psi of hydrogen overnight. Then an additional 235 mg of platinum oxide was added and shaken an additional 5 hours at 50 psi. The catalyst was filtered off, the acetic acid stripped off under reduced pressure, and the residue treated with 12% sodium hydroxide until strongly basic. The residue was then extracted with ether, and the ether extracts combined, dried over magnesium sulfate, and concentrated under reduced pressure to a brown oil (3.1 g). The product was flash chromatographed on SiO$_2$ eluting with 1% ethyl acetate/hexane. Fractions 1-9 were combined and concentrated under reduced pressure to give 710 mg of an oil. The oil was dissolved in dry ether, treated with ethereal hydrogen chloride and recrystallized from acetonitrile to give 490 mg of product as the hydrochloride salt (11% yield), mp 226.5°-227.5° C.

EXAMPLE 23 a. 1-(2-Pyrazinyl)-3-(2-pyridinyl)-2-propen-1-one (Formula (III)). An 11.5 ml (0.2 mole) portion of glacial acetic acid was added in portions to 14.1 ml (0.14 mole) of piperidine with ice cooling under N$_2$. A 35.1 g (0.33 mole) sample of pyridine-2-carboxaldehyde was added followed by 20 g (0.16 mole) of 2-acetylpyrazine. The mixture was heated on a steam bath under N$_2$ for 30 min. The reaction mixture was cooled to room temperature and 100 ml of EtOAc was added. The ethyl acetate solution was washed with 10% K$_2$CO$_3$ solution and dried (MgSO$_4$). The solvent was evaporated in vacuo. The residue was flash chromatographed on SiO$_2$ using EtOAc-hexane in 10, 20 and 30% step gradients as eluant. Fractions corresponding to the major spot were pooled and the solvent evaporated. The residue was recrystallized from 2-propanol to give 16.4 g of the title compound as a solid mp 113°–115° C.

b. 1-(2-Pyrazinyl)-3-(2-pyridinyl)-1-propanol (Formula (IV)). A 14.8 g (0.07 mole) sample of the product of Example 23a was added in portions to a suspension of 10.6 (0.28 mole) of sodium borohydride in 250 ml of 2-propanol under N$_2$. The reaction mixture was stirred for 3.5 hrs at room temperature. The mixture was acidified by cautious addition of 3N HCl then made basic by addition of 10% NaOH solution. The mixture was extracted with CHCl$_3$. The CHCl$_3$ solution was dried (MgSO$_4$) and the solvent evaporated in vacuo to give 17.6 g of the crude title compound as a brown oil.

c. 1,2,3,5,8,8a and 1,2,3,5,6,8a-Hexahydro-3-(2-pyridinyl)indolizine (Formula (VI). A 5.7 ml (0.078 mole) sample of thionyl chloride was added dropwise over 45 min to a solution of 12 g (0.056 mole) of 1-(2-pyrazinyl)-3(2-pyridinyl)-1-propanol, the product of Example 23b and 13.6 ml (0.078 mole) of ethyldiisopropylamine in 20 ml CHCl$_3$ at 5°–10° C. under nitrogen. The mixture was stirred for 2 hrs at room temperature. The solvent was evaporated in vacuo. Water (100 ml) was added. A 6.33 g (0.17 mole) sample of sodium borohydride was added in portions. The reaction was stirred for 16 hrs. The mixture was cautiously acidified with 3N HCl, then made basic by addition of 10% NaOH solution. The mixture was extracted with ether, the ether solution dried (MgSO$_4$). The solvent was evaporated in vacuo at 20 mm/Hg then 0.05 mmHg to give 3.18 g (28% yield) of the crude title compounds as a brown oil.

d. Octahydro-3-(2-pyrazinyl)indolizine Hydrochloride (Formula (I): A=2-pyrazinyl; x=0). A solution of 3.18 g of the crude product of Example 23c in 50 ml glacial acetic acid was hydrogenated over 350 mg of 5% Rh on carbon at 50 psi in a Paar Shaker for 3 hrs. The catalyst was filtered and the solvent evaporated in vacuo. The residue was partitioned between ether and 10% NaOH solution. The ether solution was dried (MgSO$_4$) and the solvent evaporated in vacuo. The residue was hydrogenated in 50 ml of MeOH over 150 mg of PtO$_2$ at 50 psi for 16 hours. The catalyst was filtered and the solvent evaporated in vacuo. The residue was chromatographed on SiO$_2$, eluting with 1% MeOH in CHCl$_3$. The fractions corresponding to the desired product were pooled and the solvent evaporated to give 800 mg (25% crude yield). A hydrochloride salt was prepared from ethereal HCl. The salt was recrystallized from CH$_3$CN to give 222 mg of the title compound as a tan solid, mp 204°–206° C.

EXAMPLE 24 a. 1-[4-8aβ-Octahydro-3α-indolizinyl)phenyl]cyclohexanol. A solution of 22 ml (220 mmoles) of 1M n-butyllithium was added dropwise to a solution of 6.0 g (21.4 m mole) of 3α-(4-bromophenyl)-8aβ-octahydroindolizine, see Example 5b, under N$_2$. After stirring for 20 min the reaction mixture was withdrawn into a syringe and added dropwise to a solution of 2.1 g of cyclohexanone in 25 ml under ether at 5° C. under N₂. The mixture was allowed to warm to room temperature and stir for 60 hrs. The reaction mixture was partitioned between water and ether. The ether layer was washed with brine, dried (K₂CO₃) and concentrated to dryness in vacuo. The residue was flash chromatographed on SiO₂ using 15% ethyl acetate-85% hexane as eluant. The fractions corresponding to the desired product were pooled and the solvent evaporated in vacuo. There was obtained 1.9 g of the title compound as an oil.

b. 3α-[4-(Cyclohexen-1-yl)phenyl]-8aβ-octahydroindolizine Hydrochloride (Formula (I): A=phenyl; R¹=1-cyclohexene; x=1). A solution of 1.9 g of 1-[4-(8aβ-octahydro-3α-indolizinyl)phenyl]cyclohexanol, the product of Example 24a, in 20 ml THF was treated with 10 ml of saturated ethereal HCl and 1 ml of water. The mixture was heated under reflux for 20 hours. The reaction mixture was washed with dilute NaOH solution and brine, dried (K₂CO₃) and concentrated to dryness in vacuo to give 1.37 g of an oil. The oil was flash chromotographed on SiO₂ with 8% ethyl acetate in hexane as the eluant. The major compound bearing fractions were pooled and the solvent evaporated in vacuo to give 1.1 g of an oil. A hydrochloride salt was prepared from ethereal HCl. It was recrystallized twice from CH₃CN to give 570 mg of the title compound as a crystalline solid, mp 225°-227° C.

EXAMPLE 25

6-[4-(8aβ-Octahydro-3α-indolizinyl)phenyl]-5-hex-yn-1-ol-cyclohexanesulfamate (1:1) (Formula (I): A=phenyl; R¹=4-CC(CH₂)₄OH; x=1). A solution of 4.0 g (14.3 mmole) of 3α-(4-bromophenyl)-8aβ-octahydroindolizine, the product of Example 5b, in 50 ml of deoxygenated triethyl amine under Ar was treated successively with 1.7 g (17.1 m mole) 5-hexyn-1-ol, 13.6 mg CuI and 177 mg of tetrakis [triphenylphosphine] palladium (0). The mixture was heated under reflux for 16 hrs. The reaction mixture was partitioned between ether and water. The ether layer was dried and the solvent evaporated in vacuo. The residue was taken up in ether and extracted with 3N HCl. The HCl solution was made basic with dilute NaOH solution. The basic solution was extracted with CHCl₃. The CHCl₃ solution was dried (K₂CO₃) and the solvent evaporated in vacuo. The residue was flash chromatographed on SiO₂ using 25% EtOAc in hexane as eluant. The major compound bearing fractions were pooled and the solvent evaporated in vacuo. The residue (2.5 g) was taken up in acetone and 1.3 g of cyclohexanesulfamic acid added. The white solid was collected by filtration and recrystallized from CH₃CN to give 2.2 g (32% yield) of the title compound as a crystalline solid mp 136°-8° C.

EXAMPLE 26

(−)-3α-(2-Bromophenyl)-8aβ-octahydroindolizine Hydrochloride (1:1). A sample of 46.7 g (0.167 mole) of (±)-3α-(2-bromophenyl)-8aβ-octahydroindolizine, the product of 1b, was combined with 67.4 g (0.167 mole) of (+)-di-p-toluoyl-D-tartaric acid monohydrate and crystallized from 900 ml of isopropanol to give 89.9 g (81%) of salt, [α]$_D^{23}$=+70.8° (0.2070 g/10 ml MeOH). The salt was recrystallized four more times from isopropanol to give 39.7 g (36%) of material m.p.=143°-144° C. (dec.) [α]$_D^{23}$=+67.8° (0.1993 g/10 ml MeOH). The salt was converted to the free base by basification with 3N NaOH and extraction into CH₂Cl₂ by stirring magnetically for 1 hr. The CH₂Cl₂ layer was washed with brine, dried (K₂CO₃) and concentrated in vacuo to give 15.74 g (94%) of residue. The residue was dissolved in MeOH, acidified with HCl gas, and recrystallized three times from MeOH/CH₃CN to give 12.46 g (24% yield) of the title compound, mp 244°-251° C., [α]$_D^{25}$=−42.6° (0.1000 g/10 ml MeOH).

EXAMPLE 27

(+)-3α-(2-Bromophenyl)-8aβ-octahydroindolizine Hydrochloride (1:1). A sample of 61.4 g (0.219 mole) of (±)-3α-(2-bromophenyl)-8aβ-octahydroindolizine, the product of Example 1b, was combined with 84.6 g (0.219 mole) of (−)-di-p-toluoyl-D-tartaric acid and crystallized from 1200 ml of isopropanol to give 99.4 g (68%) of salt, [α]$_D^{23}$=−72.6° (0.1959 g/10 ml MeOH). The salt was recrystallized five more times from isopropanol to give 30.5 g (21%) of material, mp 143°-144° C. (dec.) [α]$_D^{23}$=−68.0° (0.2007 g/10 ml MeOH). The salt was converted to the free base by basification with 3N NaOH and extraction into CH₂Cl₂ by stirring magnetically for 1 hour. The CH₂Cl₂ layer was washed with brine, dried (K₂CO₃) and concentrated in vacuo to give 11.96 g (93%) of residue. The residue was dissolved in MeOH, acidified with HCl gas, and recrystallized three times from MeOH/CH₃CN to give 9.12 g (13%) of the title compound, mp 244°-250° C., [α]$_D^{25}$=+41.0° (0.1000 g/10 ml MeOH).

What is claimed is:

1. An octahydroindolizine of the following formula (I)

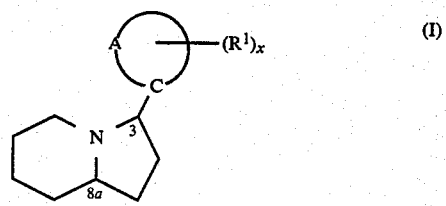

wherein

A represents the atoms necessary to form a phenyl, naphthyl, cycloalkyl, cycloalkenyl, thienyl, furanyl, pyrrolyl or pyridinyl ring system as the A-C cycle shown in formula (I);

R¹ is independently cyano, halogen, alkyl, haloalkyl, alkenyl, alkynyl, cycloalkenyl or alkyl, alkenyl or alkynyl substituted by hydroxy; and x is the integer 0, 1, 2, or 3, provided that when A is phenyl, (i) x is 1, 2 or 3, and (ii) if x is 1, R¹ is not fluoro at the para position, and the pharmaceutically-acceptable acid-addition salts thereof.

2. The octahydroindolizine of claim 1, wherein said cycloalkyl for A is cycloalkyl of about 3 to 7 carbons; said cycloalkenyl for A is cycloalkenyl of about 3 to 7 carbons; said halogen for R¹ is fluoro, chloro, bromo or iodo; the alkyl portion of said alkyl, haloalkyl and substituted alkyl for R¹ is of about 1 to 8 carbons; the alkenyl portion of said alkenyl and substituted alkenyl for R¹ is of about 2 to 8 carbons; the alkynyl portion of said alkynyl and substituted alkynyl for R¹ is of about 2 to 8 carbons; the halo portion of said haloalkyl for R¹ is one or more of fluoro, chloro, bromo or iodo atoms; and said cycloalkenyl for R¹ is cycloalkenyl of 3 to 7 carbons.

3. The octahydroindolizine of claim 1, wherein the hydrogen atoms at the 3 and 8a positions of formula (I) are cis to each other.

4. The octahydroindolizine of claim 3, wherein the hydrogen atoms at the 3 and 8a positions of formula (I) are alpha hydrogens.

5. The octahydroindolizine of claim 3, wherein the hydrogen atoms at the 3 and 8a positions of formula (I) are beta hydrogens.

6. The octahydroindolizine of claim 1, wherein the hydrogen atoms at the 3 and 8a positions of formula (I) are trans to each other.

7. The octahydroindolizine of claim 1, wherein A represents the atoms necessary to form a phenyl ring.

8. The octahydroindolizine of claim 7, wherein x is 1, 2 or 3 and at least one $R^1$ group is at the ortho position of the phenyl ring.

9. The octahydroindolizine of claim 8, wherein x is 1 and the $R^1$ group is at the ortho position of the phenyl ring.

10. The octahydroindolizine of claim 1, wherein said octahydroindolizine is selected from the group consisting of:
3-(2-bromophenyl)octahydroindolizine,
3-(1-naphthyl)octahydroindolizine,
3-(4-bromophenyl)octahydroindolizine,
3-(2-chlorophenyl)octahydroindolizine,
3-(2-methylphenyl)octahydroindolizine,
3-(2-trifluoromethylphenyl)octahydroindolizine,
3-(4-n-propylphenyl)octahydroindolizine,
3-(2,3-dichlorophenyl)octahydroindolizine,
3-(3-bromophenyl)octahydroindolizine,
3-(2,6-difluorophenyl)octahydroindolizine,
3-(2,3,4-trichlorophenyl)octahydroindolizine,
3-(2,5-dichlorophenyl)octahydroindolizine,
3-(2-chloro-6-fluorophenyl)octahydroindolizine,
3-(cyclohexyl)octahydroindolizine,
3-(2-methylcyclohexyl)octahydroindolizine,
3-(2-cyanophenyl)octahydroindolizine,
3-(2,6-dichlorophenyl)octahydroindolizine,
3-(2,5-dichloro-3-thienyl)octahydroindolizine, and
3-[4-(cyclohexen-1-yl)phenyl]octahydroindolizine,
or a pharmaceutically-acceptable acid-addition salt thereof.

11. The octahydroindolizine of claim 10, which is the 3α, 8aβ pair of enantiomers.

12. The octahydroindolizine of claim 1, which is 3α-(2-bromophenyl)-8aβ-octahydroindolizine or a pharmaceutically-acceptable acid-addition salt thereof.

13. (—)-3α-(2-Bromophenyl)-8aβ-octahydroindolizine or a pharmaceutically-acceptable acid-addition salt thereof.

14. (—)-3α-(2-Bromophenyl)-8aβ-octahydroindolizine or a pharmaceutically-acceptable acid-addition salt thereof of claim 13, wherein said salt is the hydrochloride.

15. (+)-3α-(2-Bromophenyl)-8aβ-octahydroindolizine or a pharmaceutically-acceptable acid-addition salt thereof.

16. (+)-3α-(2-Bromophenyl)-8aβ-octahydroindolizine or a pharmaceutically-acceptable acid-addition salt thereof of claim 15, wherein said salt is the hydrochloride.

17. A pharmaceutical composition effective in the treatment of pain which comprises a pharmaceutically-acceptable carrier and a pain-reducing amount of an octahydroindolizine of the following formula (I):

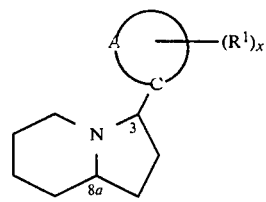

wherein
A represents the atoms necessary to form a ring system selected from the group consisting of phenyl, naphthyl, cycloalkyl, cycloalkenyl, thienyl, furanyl, pyrrolyl or pyridinyl;
$R^1$ is independently cyano, halogen, alkyl, haloalkyl, alkenyl, alkynyl, cycloalkenyl or alkyl, alkenyl or alkynyl substituted by hydroxy; and
x is the integer 0, 1, 2 or 3,
and the pharmaceutically-acceptable acid-addition salts thereof.

18. The pharmaceutical composition of claim 17 wherein said cycloalkyl for A is cycloalkyl of about 3 to 7 carbons; said cycloalkenyl for A is cycloalkenyl of about 3 to 7 carbons; said halogen for $R^1$ is fluoro, chloro, bromo or iodo; the alkyl portion of said alkyl, haloalkyl and substituted alkyl for $R^1$ is of about 1 to 8 carbons; the alkenyl portion of said alkenyl and substituted alkenyl for $R^1$ is of about 2 to 8 carbons; the alkynyl portion of said alkynyl and substituted alkynyl for $R^1$ is of about 2 to 8 carbons; the halo portion of said haloalkyl for $R^1$ is one or more of fluoro, chloro, bromo or iodo atoms; and said cycloalkenyl for $R^1$ is cycloalkenyl of 3 to 7 carbons.

19. The pharmaceutical composition of claim 17, wherein said octahydroindolizine is selected from the group consisting of:
3-(2-bromophenyl)octahydroindolizine,
3-(1-naphthyl)octahydroindolizine,
3-(4-bromophenyl)octahydroindolizine,
3-(2-chlorophenyl)octahydroindolizine,
3-(2-methylphenyl)octahydroindolizine,
3-(2-trifluoromethylphenyl)octahydroindolizine,
3-(4-n-propylphenyl)octahydroindolizine,
3-(2,4-dichlorophenyl)octahydroindolizine,
3-(3-bromophenyl)octahydroindolizine,
3-(2,6-difluorophenyl)octahydroindolizine,
3-(2,3,4-trichlorophenyl)octahydroindolizine,
3-(2,5-dichlorophenyl)octahydroindolizine,
3-(2-chloro-6-fluorophenyl)octahydroindolizine,
3-(cyclohexyl)octahydroindolizine,
3-(2-methylcyclohexyl)octahydroindolizine,
3-(2-cyanophenyl)octahydroindolizine,
3-(2,6-dichlorophenyl)octahydroindolizine,
3-(2,5-dichloro-3-thienyl)octahydroindolizine, and
3-[4-(cyclohexen-1-yl)phenyl]octahydroindolizine,
or a pharmaceutically-acceptable acid-addition salt thereof.

20. The pharmaceutical composition of claim 17, wherein said octahydroindolizine is 3α-(2-bromophenyl)-8aβ-octahydroindolizine or a pharmaceutically-acceptable acid-addition salt thereof.

21. The pharmaceutical composition of claim 17, wherein said octahydroindolizine is (—)-3α-(2-bromophenyl)-8aβ-octahydroindolizine or a pharmaceutically-acceptable acid-addition salt thereof.

22. The pharmaceutical composition of claim 17, wherein said octahydroindolizine is (+)-3α-(2-bromophenyl)-8aβ-octahydroindolizine or a pharmaceutically-acceptable acid-addition salt thereof.

23. A method of relieving pain in a mammal which comprises administering to the mammal a pharmaceutical composition effective in the treatment of pain which comprises a pharmaceutically-acceptable carrier and a pain-reducing amount of an octahydroindolizine of the following formula (I):

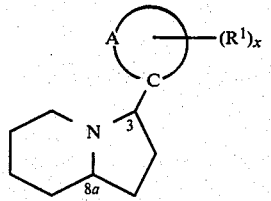

wherein

A represents the atoms necessary to form a ring system selected from the group consisting of phenyl, naphthyl, cycloalkyl, cycloalkenyl, thienyl, furanyl, pyrrolyl or pyridinyl;

$R^1$ is independently cyano, halogen, alkyl, alkyloxy, alkylthio, haloalkyl, alkenyl, alkynyl, cycloalkenyl or alkyl, alkenyl or alkynyl substituted by hydroxy; and x is the integer 0, 1, 2 or 3, and the pharmaceutically-acceptable acid-addition salts thereof.

24. The method of claim 23, wherein said mammal is a human.

25. The method of claim 23, wherein said cycloalkyl for A is cycloalkyl of about 3 to 7 carbons; said cycloalkenyl for A is cycloalkenyl of about 3 to 7 carbons; said halogen for $R^1$ is fluoro, chloro, bromo or iodo; the alkyl portion of said alkyl, alkyloxy, alkylthio, haloalkyl and substituted alkyl for $R^1$ is of about 1 to 8 carbons; the alkenyl portion of said alkenyl and substituted alkenyl for $R^1$ is of about 2 to 8 carbons; the alkynyl portion of said alkynyl and substituted alkynyl for $R^1$ is of about 2 to 8 carbons; the halo portion of said haloalkyl for $R^1$ is one or more of fluoro, chloro, bromo or iodo atoms; and said cycloalkenyl for $R^1$ is cycloalkenyl of 3 to 7 carbons.

26. The method of claim 23, wherein said octahydroindolizine is selected from the group consisting of:
3-(2-bromophenyl)octahydroindolizine,
3-(3-methoxyphenyl)octahydroindolizine,
3-(2-methoxyphenyl)octahydroindolizine,
3-(1-naphthyl)octahydroindolizine,
3-(4-bromophenyl)octahydroindolizine,
3-(2-chlorophenyl)octahydroindolizine,
3-(2-methylphenyl)octahydroindolizine,
3-(2-trifluoromethylphenyl)octahydroindolizine,
3-(4-n-propylphenyl)octahydroindolizine,
3-(2,4-dichlorophenyl)octahydroindolizine,
3-(3-bromophenyl)octahydroindolizine,
3-(2,6-difluorophenyl)octahydroindlizine,
3-(2,3,4-trichlorophenyl)octahydroindolizine,
3-(2,5-dichlorophenyl)octahydroindolizine,
3-(2-chloro-6-fluorophenyl)octahydroindolizine,
3-(cyclohexyl)octahydroindolizine,
3-(2-methylcyclohexyl)octahydroindolizine,
3-[2-(methylthio)phenyl]octahydroindolizine,
3-(2-cyanophenyl)octahydroindolizine,
3-(2,6-dichlorophenyl)octahydroindolizine,
3-(2,5-dichloro-3-thienyl)octahydroindolizine, and
3-[4-(cyclohexen-1-yl)phenyl]octahydroindolizine,
or a pharmaceutically-acceptable acid-addition salt thereof.

27. The method of claim 23, wherein said octahydroindolizine is 3α-(2-bromophenyl)-8aβ-octahydroindolizine or a pharmaceutically-acceptable acid-addition salt thereof.

28. The method of claim 28, wherein said octahydroindolizine is (−)-3α-(2-bromophenyl)-8aβ-octahydroindolizine or a pharmaceutically-acceptable acid-addition salt thereof.

29. The method of claim 23, wherein said octahydroindlizine is (+)-3α-(2-bromophenyl)-8aβ-octahydroindolizine or a pharmaceutically-acceptable acid-addition salt thereof.

* * * * *